(12) United States Patent
Yuhas et al.

(10) Patent No.: US 10,878,943 B2
(45) Date of Patent: Dec. 29, 2020

(54) CRYSTALLINE METALLOPHOSPHATES, THEIR METHOD OF PREPARATION, AND USE

(71) Applicant: UOP LLC, Des Plaines, IL (US)

(72) Inventors: Benjamin D. Yuhas, Evanston, IL (US); Kristine N. Wilson, Elgin, IL (US); Mark A. Miller, Niles, IL (US); Mimoza Sylejmani-Rekaliu, Bensenville, IL (US); John P. S. Mowat, Arlington Heights, IL (US)

(*) Notice: Subject to any disclaimer, the term of this patent is extended or adjusted under 35 U.S.C. 154(b) by 224 days.

(21) Appl. No.: 16/129,670

(22) Filed: Sep. 12, 2018

(65) Prior Publication Data

US 2019/0392113 A1    Dec. 26, 2019

Related U.S. Application Data

(63) Continuation-in-part of application No. 16/015,115, filed on Jun. 21, 2018, now Pat. No. 10,662,069.

(51) Int. Cl.
| | |
|---|---|
| *G01N 23/20* | (2018.01) |
| *G16C 20/10* | (2019.01) |
| *C01B 39/54* | (2006.01) |
| *G16C 20/20* | (2019.01) |

(52) U.S. Cl.
CPC ............. *G16C 20/10* (2019.02); *C01B 39/54* (2013.01); *G01N 23/20075* (2013.01); *G16C 20/20* (2019.02); *C01P 2002/72* (2013.01); *C01P 2004/03* (2013.01)

(58) Field of Classification Search
CPC ...... B01J 23/8913; B01J 23/74; B01J 37/031; B01J 29/84; B01J 29/83; C01P 2002/72; C01B 39/54
See application file for complete search history.

(56) References Cited

U.S. PATENT DOCUMENTS

| | | | | |
|---|---|---|---|---|
| 4,440,871 A | * | 4/1984 | Lok ...................... | C07C 5/2716 502/214 |
| 8,569,557 B1 | * | 10/2013 | Lewis ...................... | C07C 2/66 585/455 |
| 8,747,807 B2 | * | 6/2014 | Jan .......................... | C01B 39/48 208/135 |

(Continued)

*Primary Examiner* — Shogo Sasaki

(57) ABSTRACT

A family of crystalline microporous metallophosphates designated AlPO-90 has been synthesized represented by the empirical formula $$R^+_r M_m^{2+} E P_x Si_y O_z$$

where R is an organoammonium cation, M is a framework metal alkaline earth or transition metal of valence +2, and E is a trivalent framework element such as aluminum or gallium. The compositions are characterized by a new unique ABC-6 net structure, and have catalytic properties for various hydrocarbon conversion processes, and characteristics suitable for efficient adsorption of water vapor in a variety of applications, including adsorption heat pumps. A parameter data system comprising at least one processor; at least one memory storing computer-executable instructions; and at least one receiver configured to receive data of a parameter of a data of a parameter of at least one unit or stream in fluid communication with and downstream from or upstream to a conversion process comprising at least one reaction catalyzed by SAPO-90.

19 Claims, 5 Drawing Sheets

(56) References Cited

U.S. PATENT DOCUMENTS

| | | | |
|---|---|---|---|
| 8,911,614 B2 * | 12/2014 | Lewis | C07C 1/20 208/108 |
| 8,936,776 B2 * | 1/2015 | Lewis | C01B 39/54 423/277 |
| 2019/0389733 A1 * | 12/2019 | Yuhas | B01D 53/02 |

* cited by examiner

CRYSTALLINE METALLOPHOSPHATES, THEIR METHOD OF PREPARATION, AND USE

CROSS-REFERENCE TO RELATED APPLICATION

This application is a Continuation-In-Part of granted U.S. patent Ser. No. 10/662,069 issued May 26, 2020, the contents of which cited patent are hereby incorporated by reference in its entirety.

BACKGROUND OF THE INVENTION

This invention relates to a novel family of metallophosphates, collectively designated AlPO-90. They are represented by the empirical formula:

$$C_c^+ A_a^+ M_m^{2+} E P_x Si_y O_z$$

where M is a divalent framework metal such as magnesium or zinc, C is a cyclic organoammonium cation, A is an acyclic organoammonium cation, and E is a trivalent framework element such as aluminum or gallium.

Classes of molecular sieves include crystalline aluminophosphate, silicoaluminophosphate, or metalloaluminophosphate compositions which are microporous and which are formed from corner sharing $AlO_{4/2}$ and $PO_{4/2}$ tetrahedra. In 1982, Wilson et al. first reported aluminophosphate molecular sieves, the so-called AlPOs, which are microporous materials that have many of the same properties as zeolites, although they do not contain silica (See U.S. Pat. No. 4,310,440). Subsequently, charge was introduced to the neutral aluminophosphate frameworks via the substitution of $SiO_{4/2}$ tetrahedra for $PO_{4/2}^+$ tetrahedra to produce the SAPO molecular sieves as described by Lok et al. (See U.S. Pat. No. 4,440,871). Another way to introduce framework charge to neutral aluminophosphates is to substitute $[Me^{2+}O_{4/2}]^{2-}$ tetrahedra for $AlO_{4/2}^-$ tetrahedra, which yields the MeAPO molecular sieves (see U.S. Pat. No. 4,567,029). It is furthermore possible to introduce framework charge on AlPO-based molecular sieves via the simultaneous introduction of $SiO_{4/2}$ and $[M^{2+}O_{4/2}]^{2-}$ tetrahedra to the framework, giving MeAPSO molecular sieves (See U.S. Pat. No. 4,973,785).

Numerous molecular sieves, both naturally occurring and synthetically prepared, are used in various industrial processes. Synthetically, these molecular sieves are prepared via hydrothermal synthesis employing suitable sources of Si, Al, P, metals, and structure directing agents such as amines or organoammonium cations. The structure directing agents reside in the pores of the molecular sieve and are largely responsible for the particular structure that is ultimately formed. These species may balance the framework charge associated with silicon or other metals such as Zn or Mg in the aluminophosphate compositions, and can also serve as space fillers to stabilize the tetrahedral framework. A particular synthetic scheme utilizes multiple structure-directing agents in the same gel in order to direct the formation of multiple cages or cavities. This has been demonstrated for aluminosilicates, such as UZM-5 (U.S. Pat. No. 8,747,807), as well as silicoaluminophosphates, such as STA-20 (Turrina et al., *Chem. Mater.*, 29, 2180 (2017)).

Molecular sieves are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent molecular sieve crystal structure. Molecular sieves can be used for separation applications, in which certain species of a mixed liquid or vapor stream are captured within the pores of the molecular sieve, and others are excluded. Molecular sieves can also be used as catalysts for hydrocarbon conversion reactions, which can take place on outside surfaces as well as on internal surfaces within the pore.

As stated above, molecular sieves are capable of reversibly adsorbing and desorbing certain molecules depending on the adsorbate's size and the molecular sieve's internal pore structure. There are many applications where it is desired to adsorb water vapor, preferably in a reversible manner. One such application is an adsorption heat pump, which is a device that can be used to recover energy from exhaust or waste heat. As such, adsorption heat pumps can be utilized to maximize energy efficiency in an environmentally friendly manner. Molecular sieves can be useful materials to act as water vapor adsorbents in an adsorption heat pump due to their high capacity for water vapor. A description of the use of adsorbents in adsorption heat pumps can be found in U.S. Pat. No. 8,323,747, incorporated by reference herein in its entirety.

The type of molecular sieves used in adsorption heat pumps must meet certain requirements for optimal performance. A high overall capacity for water vapor is important, but most critically, they should fully desorb all adsorbed water at no greater than 100° C. Otherwise, too much heat must be applied to fully remove the adsorbed water from the micropores (i.e., the regeneration temperature is too high), thus requiring too high of an energy input. The majority of aluminosilicates (i.e., zeolites) have rapid uptake of water vapor at very low pressures ($P/P_0$), which conversely leads to an unacceptably high regeneration temperature, despite a high overall capacity for water vapor. Aluminophosphates and silicoaluminophosphates have been shown to have more favorable adsorption characteristics for water vapor (see, for example, M. F. de Lange et al. *Chem. Rev.* 115, 12205 (2015); H. van Heyden et al. *Appl. Therm. Eng.* 29, 1514 (2009). In particular, the materials SAPO-34 and SAPO-5 (zeotypes CHA and AFI, respectively) have been shown to have particular utility as adsorbent materials in adsorption heat pumps (see U.S. Pat. Nos. 7,422,993, 9,517,942).

SUMMARY OF THE INVENTION

As stated, the present invention relates to a new family of metallophosphate molecular sieves, collectively designated AlPO-90. Accordingly, one embodiment of the invention is a microporous crystalline material having a three-dimensional framework of at least $EO_{4/2}^-$ and $PO_{4/2}^+$ tetrahedral units and optionally, at least one of $[M^{2+}O_{4/2}]^{2-}$ and $SiO_{4/2}$ tetrahedral units and an empirical composition in the as-synthesized form and anhydrous basis expressed by an empirical formula of:

$$C_c^+ A_a^+ M_m^{2+} E P_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, C is a cyclic organoammonium cation, and A is an acyclic organoammonium cation. The ratio c/a can have a value from 0.01 to about 100, and the sum (c+a) represents the mole ratio of (C+A) to E and has a value of about 0.1 to about 2.0. E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z=(2 \cdot m+c+a+3+5 \cdot x+4 \cdot y)/2$$

The invention is characterized in that it has the x-ray diffraction pattern having at least the d-spacings and intensities set forth in Table 1:

TABLE 1

| 2-theta(°) | d (Å) | Intensity |
|---|---|---|
| 9.86-9.91 | 8.96-8.91 | w-m |
| 13.97-14.10 | 6.34-6.28 | m |
| 17.21-17.26 | 5.15-5.13 | vw-w |
| 18.79-18.91 | 4.72-4.68 | vw-w |
| 19.78-19.87 | 4.49-4.46 | m-s |
| 22.19-22.33 | 4.01-3.97 | w-m |
| 23.57-23.63 | 3.78-3.76 | w |
| 24.36-24.50 | 3.66-3.63 | vs |
| 27.55-27.61 | 3.24-3.22 | w-m |
| 28.16-28.37 | 3.17-3.14 | m |
| 31.51-31.69 | 2.84-2.82 | w-m |
| 33.26-33.37 | 2.70-2.68 | vw |
| 34.32-34.86 | 2.62-2.57 | w-m |
| 42.59-42.91 | 2.13-2.10 | vw-w |
| 47.70-47.90 | 1.91-1.89 | vw-w |
| 51.92-52.37 | 1.76-1.74 | w-m |

Another embodiment of the invention is a microporous crystalline material having a three-dimensional framework of at least $EO_{4/2}^-$ and $PO_{4/2}^+$ tetrahedral units and optionally, at least one of $[M^{2+}O_{4/2}]^{2-}$ and $SiO_{4/2}$ tetrahedral units and an empirical composition in the calcined form and anhydrous basis expressed by an empirical formula of:

$$H_w M_m^{2+} EP_x Si_y O_z$$

where "m", "x", "y" are as described above, H is a proton, "w" is the mole ratio of H to E and varies from 0 to 2.5, and "z" is the mole ratio of O to E and has a value determined by the equation:

$$z=(w+2 \cdot m+3+5 \cdot x+4 \cdot y)/2$$

and the invention is characterized in that it has the x-ray diffraction pattern having at least the d-spacings and intensities set forth in Table 2:

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

Another embodiment of the invention is a process for preparing the crystalline microporous metallophosphate molecular sieve described above. The process comprises forming a reaction mixture containing reactive sources of C, A, E, P, one or both of M and Si, and heating the reaction mixture at a temperature of about 60° C. to about 200° C. for a time sufficient to form the molecular sieve, the reaction mixture having a composition expressed in terms of mole ratios of the oxides of:

$$aA_2O{:}bC_2O{:}cMO{:}E_2O_3{:}dP_2O_5{:}eSiO_2{:}fH_2O$$

where "a" has a value of about 0.01 to about 5, "b" has a value of about 0.01 to about 5, "c" has a value of about 0 to about 2, "d" has a value of about 0.5 to about 8, "e" has a value of about 0 to about 4, and "f" has a value from 30 to 1000.

Yet another embodiment of the invention is a hydrocarbon conversion process using the above-described molecular sieve as a catalyst. The process comprises contacting at least one hydrocarbon with the molecular sieve at conversion conditions to generate at least one converted hydrocarbon.

Still another embodiment of the invention is an adsorption process using the crystalline AlPO-90 material. The process may involve the adsorption and desorption of water vapor over AlPO-90 in an adsorption heat pump-type apparatus. Separation of molecular species can be based either on the molecular size (kinetic diameter) or on the degree of polarity of the molecular species. Removing contaminants may be by ion exchange with the molecular sieve.

Yet another embodiment is a parameter data system comprising at least one processor; at least one memory storing computer-executable instructions; and at least one receiver configured to receive data of a parameter of at least one unit or stream in fluid communication with, and downstream from or upstream to a hydrocarbon conversion process using the above-described molecular sieve as a catalyst. The process comprises contacting at least one hydrocarbon with the molecular sieve at conversion conditions to generate at least one converted hydrocarbon.

Yet another embodiment is a parameter data system comprising at least one processor; at least one memory storing computer-executable instructions; and at least one receiver configured to receive data of a parameter of at least one unit or stream in fluid communication with, and downstream from or upstream to an adsorption process using the crystalline AlPO-90 material. The process may involve the adsorption and desorption of water vapor over AlPO-90 in an adsorption heat pump-type apparatus. Separation of molecular species can be based either on the molecular size (kinetic diameter) or on the degree of polarity of the molecular species. Removing contaminants may be by ion exchange with the molecular sieve.

The system may further comprise an Input/Output device to collect the data. The system may have the processor configured to evaluate the data. The system may have the processor is configured to correlate the data. The system may further comprise a transmitter to transmit a signal to the conversion process. The signal may comprise instructions. The signal may comprise instructions regarding an adjustment to a parameter. The system may further comprise collecting data from multiple systems wherein one system is the parameter data system. The processor may be configured to generate predictive information. The processor may be configured to generate quantitative information.

Yet another embodiment is a method for collecting data from a conversion process, the method comprising receiving data from at least one sensor of least one unit or stream in fluid communication with, and downstream from or upstream to, a conversion process, the conversion process comprising at least one reaction catalyzed by a material comprising is a microporous crystalline material having a three-dimensional framework of at least $EO_{4/2}^-$ and $PO_{4/2}^+$ tetrahedral units and optionally, at least one of $[M^{2+}O_{4/2}]^{2-}$ and $SiO_{4/2}$ tetrahedral units and an empirical composition in the as-synthesized form and anhydrous basis expressed by an empirical formula of:

$$C_c^+ A_a^+ M_m^{2+} EP_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, C is a cyclic organoammonium cation, and A is an acyclic organoammonium cation. The ratio c/a can have a value from 0.01 to about 100, and the sum (c+a) represents the mole ratio of (C+A) to E and has a value of about 0.1 to about 2.0. E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z=(2 \cdot m+c+a+3+5 \cdot x+4 \cdot y)/2.$$

The at least one unit or stream may or may not be in direct fluid communication with the conversion process. Intervening units or streams may be present. The method may further comprise at least one of displaying or transmitting or analyzing the received data. The method may further comprise analyzing the received data to generate at least one instruction and transmitting the at least one instruction. The method may further comprise analyzing the received data and generating predictive information. The method may further comprise analyzing the received data and generating quantitative information.

Additional features and advantages of the invention will be apparent from the description of the invention, figures and claims provided herein.

DETAILED DESCRIPTION OF THE INVENTION

Figure 1:
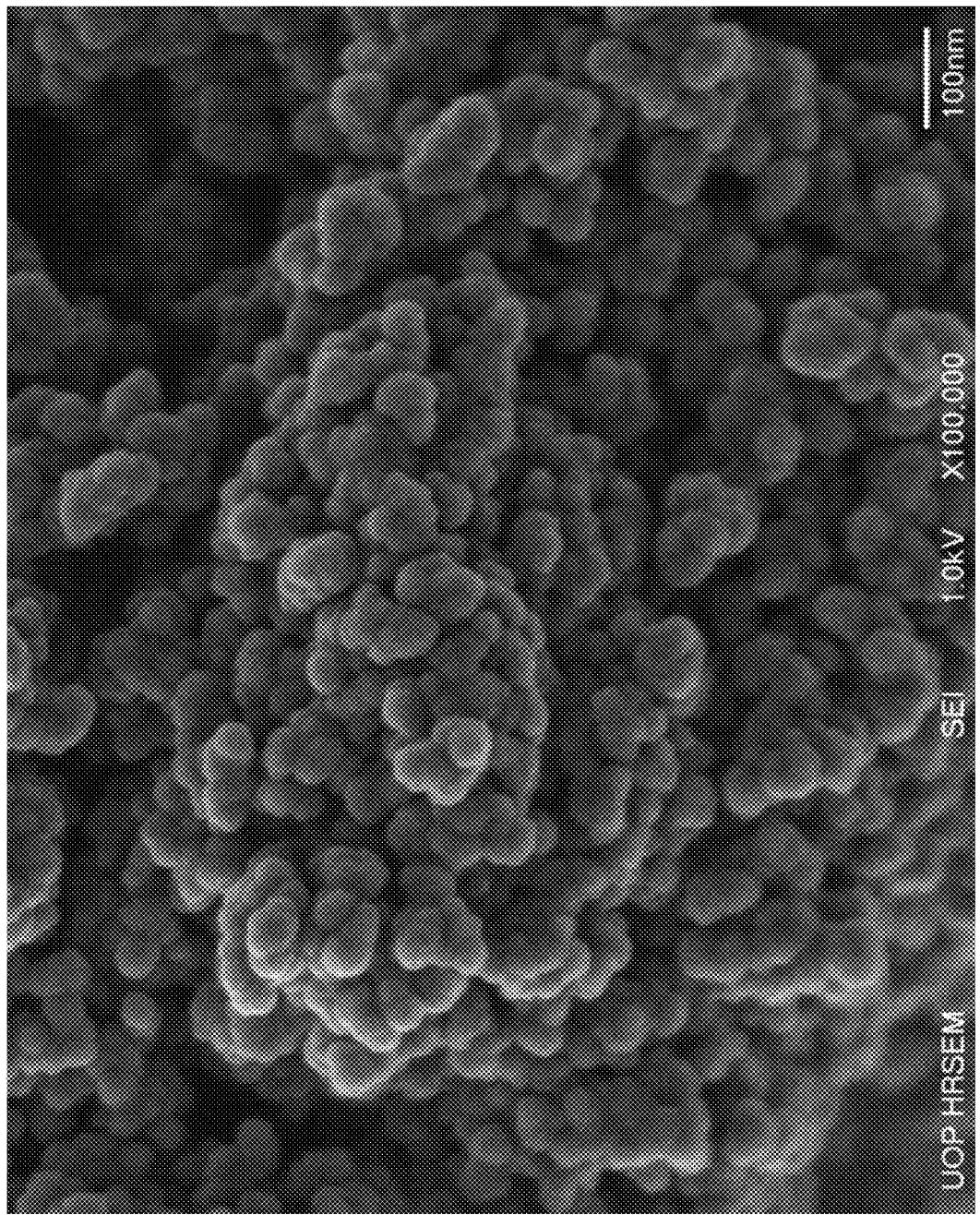
FIG. 1 is a scanning electron microscope (SEM) image of an exemplary AlPO-90 material according to an embodiment described herein.
Figure 2:
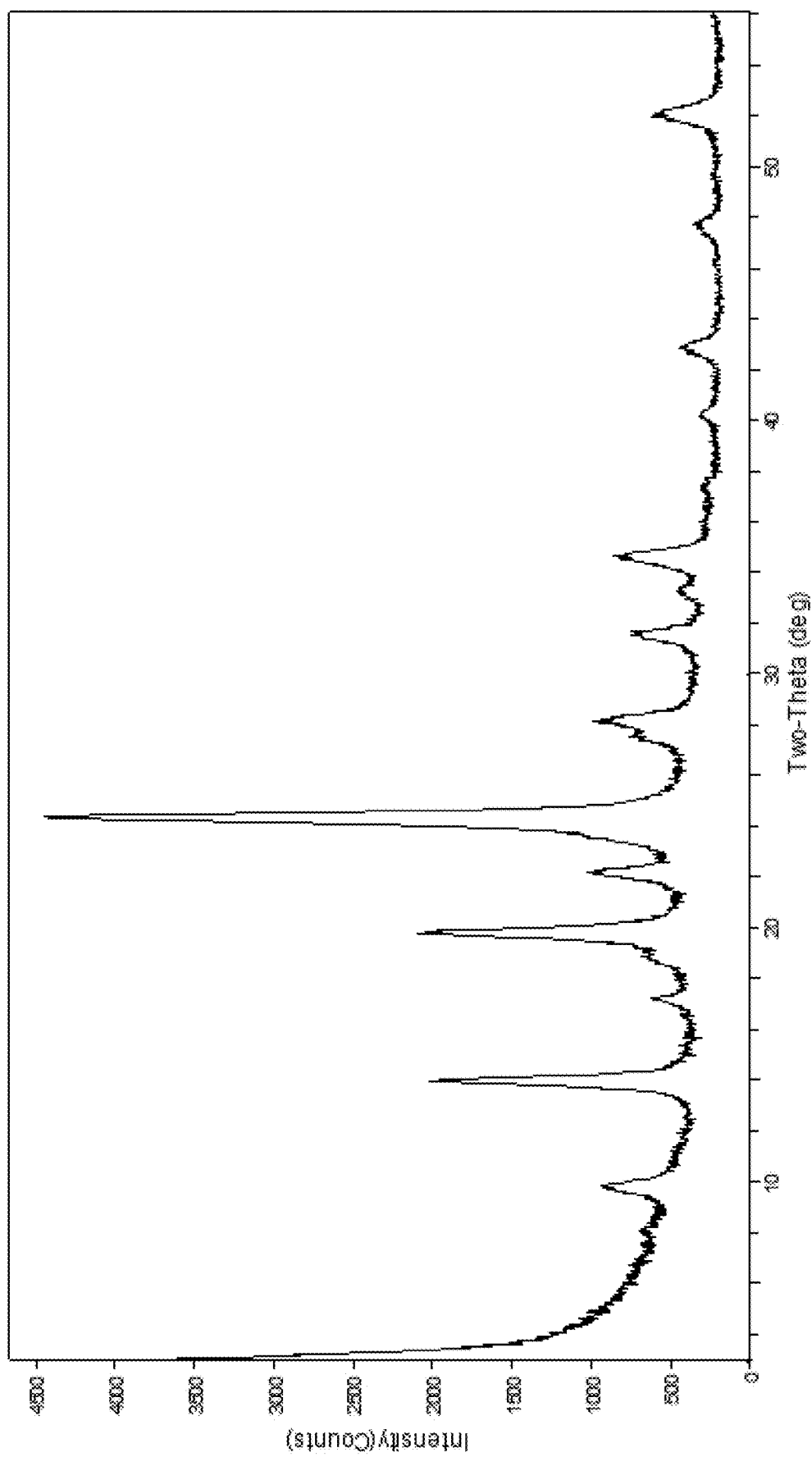
FIG. 2 is an x-ray diffraction pattern of an exemplary AlPO-90 material in the as-synthesized form.

The invention relates to a parameter data system comprising at least one processor; at least one memory storing computer-executable instructions; and at least one receiver configured to receive data of at least one parameter of at least one unit or stream in fluid communication with and downstream from or upstream to a conversion process comprising at least one reaction catalyzed by a material comprising AlPO-90 that is thermally stable upon calcination, and may be characterized by the x-ray diffraction pattern, having at least the d-spacings and relative intensities set forth in Table 2 below:

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |

TABLE 2-continued

| 2-theta(°) | d (Å) | Intensity |
|---|---|---|
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

The stable calcined AlPO-90 material can be characterized on an anhydrous basis by the empirical formula:

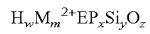

$$H_w M_m^{2+} E P_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z=(w+2 \cdot m+3+5 \cdot x+4 \cdot y)/2.$$

The at least one unit or stream may or may not be in direct fluid communication with the conversion process. Intervening units or streams may be present. The system may further comprise an Input/Output device to collect the data. The system may have the processor configured to evaluate the data. The system may have the processor is configured to correlate the data. The system may further comprise a transmitter to transmit a signal to the conversion process. The signal may comprise instructions. The signal may comprise instructions regarding an adjustment to a parameter. The system may further comprise collecting data from multiple systems wherein one system is the parameter data system. The processor may be configured to generate predictive information. The processor may be configured to generate quantitative information. The conversion process may be a refinery conversion process or a petrochemical conversion process.

The invention also relates to a method for collecting data from a conversion process, the method comprising receiving data from at least one sensor of least one unit or stream in fluid communication with and downstream from or upstream to a conversion process, the conversion process comprising at least one reaction catalyzed by a material comprising AlPO-90 that is thermally stable upon calcination, and may be characterized by the x-ray diffraction pattern, having at least the d-spacings and relative intensities set forth in Table 2 below:

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |

TABLE 2-continued

| 2-theta(°)  | d (Å)     | Intensity |
|-------------|-----------|-----------|
| 35.05-35.12 | 2.56-2.55 | w         |
| 52.60-52.81 | 1.74-1.73 | vw        |

The stable calcined AlPO-90 material can be characterized on an anhydrous basis by the empirical formula:

$$H_w M_m^{2+} EP_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z=(w+2\cdot m+3+5\cdot x+4\cdot y)/2.$$

The at least one unit or stream may or may not be in direct fluid communication with the conversion process. Intervening units or streams may be present. The method may further comprise at least one of displaying or transmitting or analyzing the received data. The method may further comprise analyzing the received data to generate at least one instruction and transmitting the at least one instruction. The method may further comprise analyzing the received data and generating predictive information. The method may further comprise analyzing the received data and generating quantitative information. The conversion process may be a refinery conversion process or a petrochemical conversion process.

Applicants have prepared a family of metallophosphate materials whose topological structure is unique. In their paper "Enumeration of 4-connected 3-dimensional nets and classification of framework silicates: the infinite set of ABC-6 nets; the Archimedean and σ-related nets," Smith and Bennett state "To a first approximation, all silicates belonging to the ABC-6net family have x-ray diffraction patterns which can be indexed on a hexagonal prismatic unit cell with lattice parameters a ~13.0±0.3 Å and c~p×(2.6±0.1 Å)." (See American Mineralogist, 66, 777-788 (1981)). This finding has subsequently been confirmed by others (see, for example, D. Xie et al. *J. Am. Chem. Soc.* 135, 10519 (2013)) as the ABC-6 family has expanded.

One particular composition of AlPO-90 indexes on a unit cell with hexagonal axes with lattice parameters a=12.559 Å and c=15.333 Å, which is suggests an ABC-6 net structure with the stacking sequence repeating every 6 layers along the c-axis (p=15.333/2.5=6.13). In the prior art, Meier and Groner enumerated the 10 possible stacking sequences for a 6-layer molecular sieve with hexagonal symmetry in 1981 (*J. Solid State Chem.*, 37, 204 (1981)). This finding was later confirmed by Li et al. in 2015 (*Nat. Commun.* 2015, 6, 8328). At the time of these publications, only 4 of the 10 possible 6-layer stacking sequences had been experimentally realized in the prior art (zeotypes CHA, ERI, LIO, and EAB). Because there are many potential stacking sequences possible for a given ABC-6 material, the fact that a material has similar lattice parameters to a known material in the prior art does not automatically imply that the two materials are identical. Through a combination of x-ray diffraction experimental techniques as well as modeling, applicants have determined that AlPO-90 can be described as a combination of two novel zeotypes, which have stacking sequences of AABCBC and ABACBC. Although these zeotypes have been theoretically predicted to exist, the instant material AlPO-90, with its unique topological connectivity, represents the first experimental realization of these structures.

The instant microporous crystalline material (AlPO-90) has an empirical composition in the as-synthesized form and on an anhydrous basis expressed by the empirical formula:

$$C_c^+ A_a^+ M_m^{2+} EP_x Si_y O_z$$

where M is at least one framework divalent cation and is selected from the group consisting of alkaline earth and transition metals. Specific examples of the M cations include but are not limited to beryllium, magnesium, cobalt (II), manganese, zinc, iron(II), nickel and mixtures thereof. C is a cyclic organoammonium cation, and A is an acyclic organoammonium cation. The ratio c/a can have a value from 0.01 to about 100, and the sum (c+a) represents the mole ratio of (C+A) to E and has a value of about 0.1 to about 2.0. The value of "m" is the mole ratio of M to E and varies from 0 to about 1.0, "x" is mole ratio of P to E and varies from 0.5 to about 2.0. The ratio of silicon to E is represented by "y" which varies from about 0 to about 1.0. E is a trivalent element which is tetrahedrally coordinated, is present in the framework, and is selected from the group consisting of aluminum, gallium, iron(III) and boron. Lastly, "z" is the mole ratio of O to E and is given by the equation:

$$z=(2\cdot m+r+3+5\cdot x+4\cdot y)/2.$$

Synthesis of molecular sieve materials often relies on the use of organoamino or organoammonium templates known as organic structure directing agents (OSDAs). While simple OSDAs such as tetramethylammonium, tetraethylammonium and tetrapropylammonium are commercially available, oftentimes OSDAs are complicated molecules that are difficult and expensive to synthesize. However, their importance lies in their ability to impart aspects of their structural features to the molecular sieve to yield a desirable pore structure. For example, the use of 1,4,7,10,13,16-hexamethyl-1,4,7,10,13,16-hexaazacyclooctadecane as OSDA has been shown to allow synthesis of STA-7, an aluminophosphate based material of the SAV zeotype (Wright et. al. *J. Chem. Soc., Dalton Trans.*, 2000, 1243-1248); the use of 4,7,13,16,21,24-hexaoxa-1,10-diazabicyclo[8.8.8]hexacosane ('Kryptofix 222') led to the synthesis of AlPO4-42 (Schreyeck et. al. *Micro. Meso. Mater.* 1998, 22, 87-106); MAPO-35, a magnesium aluminophosphate material with the LEV topology, is disclosed in U.S. Pat. No. 4,567,029 in which quinuclidine is employed as a structure directing agent; and in U.S. Pat. No. 4,973,785, the MeAPSO composition CoAPSO-35 is disclosed, which contains both cobalt and silicon in the framework in addition to Al and P and uses methylquinuclidine as the structure directing agent.

The art clearly shows that use of complex organoammonium SDAs often results in new molecular sieve materials. However, the synthesis of these complicated organoammonium compounds is quite lengthy and requires many steps, often in an organic solvent, thereby hindering development of the new molecular sieve material. Frequently, even for simple, commercially available OSDAs, the OSDA is the most costly ingredient used in synthesizing molecular sieve materials. Consequently, it would be economically advantageous to synthesize new molecular sieves from either commercially available organoammonium SDAs or SDAs which may be readily synthesized from commercially available starting materials. This has recently been demonstrated in an elegant fashion using simple aqueous chemistry to generate a novel family of organo-1-oxa-4-azonium cyclohexane compounds (U.S. Pat. No. 9,522,896), derived from morpholino-based compounds. The procedures described in U.S. Pat. No. 9,522,896 can be extended to the family of piperidine-based compounds as well. This procedure thereby allows the preparation of SDAs, such as unusual quaternary ammonium salts, from readily available starting reagents in a facile and practical manner. OSDAs prepared by the methods of the present invention are in aqueous solution and do not pose odor and flashpoint concerns. The result is the unprecedented ability to remove the cooling step typically required in the preparation of in-situ zeolite reaction mixtures and to avoid purification steps such as evaporation of organic solvent typically required in ex-situ preparation methods. The obtained organoammonium bromide salt can be ion-exchanged, either by reaction with $Ag_2O$ or by anion exchange resins to yield the hydroxide form of the organoammonium compound, or used as the halogen salt directly. Finally, the resultant organoammonium compound can be used for the synthesis of a zeolite or molecular sieve.

The microporous crystalline metallophosphate AlPO-90 is prepared by a hydrothermal crystallization of a reaction mixture prepared by combining reactive sources of C, A, E, phosphorus, and one or both of M and silicon. A preferred form of the AlPO-90 materials is when E is Al. The sources of aluminum include but are not limited to aluminum alkoxides, precipitated aluminas, aluminum metal, aluminum hydroxide, aluminum salts and alumina sols. Specific examples of aluminum alkoxides include, but are not limited to aluminum ortho sec-butoxide and aluminum ortho isopropoxide. Sources of phosphorus include, but are not limited to, orthophosphoric acid, phosphorus pentoxide, and ammonium dihydrogen phosphate. Sources of silica include but are not limited to tetraethylorthosilicate, colloidal silica, and precipitated silica. Sources of the other E elements include but are not limited to organoammonium borates, boric acid, precipitated gallium oxyhydroxide, gallium sulfate, ferric sulfate, and ferric chloride. Sources of the M metals include the halide salts, nitrate salts, acetate salts, and sulfate salts of the respective alkaline earth and transition metals.

One component of C may be an organoammonium cation prepared from the reaction of an aqueous mixture of a cyclic secondary amine and an organic dihalide. Specific examples of cyclic secondary amines include, without limitation, piperidine, homopiperidine, pyrrolidine, and morpholine. Specific examples of organic dihalides include, without limitation, 1,4-dibromobutane, 1,5-dibromopentane, and 1,6-dibromohexane.

In one embodiment, the cyclic secondary amine is piperidine and the organic dihalide is 1,4-dibromobutane. In another embodiment, the cyclic secondary amine is piperidine and the organic dihalide is 1,4-dibromopentane. In another embodiment, the cyclic secondary amine is piperidine and the organic dihalide is 1,5-dibromopentane. In another embodiment, the cyclic secondary amine is pyrrolidine and the organic dihalide is 1,4-dibromobutane.

One component of A may be a tetraalkylammonium cation, represented as $NR_4^+$. The R groups are chosen such that is the cation A is acyclic, and there may be multiple distinct R groups on the same quaternary nitrogen. A particular R group may have the formula $C_nH_{2n+1}$, where n is a whole number ranging from 1 to 4, inclusive. Non-limiting examples of component A include tetramethylammonium, ethyltrimethylammonium, diethyldimethylammonium, methyltriethylammonium, tetraethylammonium, tetrapropylammonium, propyltrimethylammonium, butyltrimethylammonium, dipropyldimethylammonium, and methylethyldipropylammonium.

The reaction mixture containing reactive sources of the desired components can be described in terms of molar ratios of the oxides by the formula:

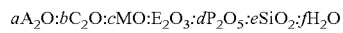

$$aA_2O:bC_2O:cMO:E_2O_3:dP_2O_5:eSiO_2:fH_2O$$

where "a" has a value of about 0.01 to about 5, "b" has a value of about 0.01 to about 5, "c" has a value of about 0 to about 2, "d" has a value of about 0.5 to about 8, "e" has a value of about 0 to about 4, and "f" has a value from 30 to 1000. If alkoxides are used, it is preferred to include a distillation or evaporative step to remove the alcohol hydrolysis products.

The reaction mixture is reacted at a temperature of about 60° C. to about 200° C. and preferably from about 125° C. to about 175° C. for a period of about 1 day to about 21 days and preferably for a time of about 2 days to about 10 days in a sealed reaction vessel at autogenous pressure. The reaction vessel may be heated with stirring, heated while tumbling, or heated quiescently. After crystallization is complete, the solid product is isolated from the heterogeneous mixture by means such as filtration or centrifugation, and then washed with deionized water and dried in air at ambient temperature up to about 100° C. AlPO-90 seeds can optionally be added to the reaction mixture in order to accelerate the formation of the desired microporous composition.

The AlPO-90 aluminophosphate-based material, which is obtained from the above-described process, is characterized by the x-ray following diffraction pattern, having at least the d-spacings and relative intensities set forth in Table 1:

TABLE 1

| 2-theta(°) | d (Å) | Intensity |
|---|---|---|
| 9.86-9.91 | 8.96-8.91 | w-m |
| 13.97-14.10 | 6.34-6.28 | m |
| 17.21-17.26 | 5.15-5.13 | vw-w |
| 18.79-18.91 | 4.72-4.68 | vw-w |
| 19.78-19.87 | 4.49-4.46 | m-s |
| 22.19-22.33 | 4.01-3.97 | w-m |
| 23.57-23.63 | 3.78-3.76 | w |
| 24.36-24.50 | 3.66-3.63 | vs |
| 27.55-27.61 | 3.24-3.22 | w-m |
| 28.16-28.37 | 3.17-3.14 | m |
| 31.51-31.69 | 2.84-2.82 | w-m |
| 33.26-33.37 | 2.70-2.68 | vw |
| 34.32-34.86 | 2.62-2.57 | w-m |
| 42.59-42.91 | 2.13-2.10 | vw-w |
| 47.70-47.90 | 1.91-1.89 | vw-w |
| 51.92-52.37 | 1.76-1.74 | w-m |

The AlPO-90 material may be calcined in either air or nitrogen to remove the occluded template. In one embodiment of the invention, the AlPO-90 is calcined at a temperature of at least 550° C. In another embodiment of the invention, the AlPO-90 is calcined at a temperature of at least 600° C. In another embodiment of the invention, the AlPO-90 is calcined at a temperature of at least 650° C. The AlPO-90 is thermally stable upon calcination, and may be characterized by the x-ray diffraction pattern, having at least the d-spacings and relative intensities set forth in Table 2 below:

TABLE 2

| 2-theta(°) | d (Å) | Intensity |
| --- | --- | --- |
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

The stable calcined AlPO-90 material can be characterized on an anhydrous basis by the empirical formula:

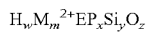

$$H_w M_m^{2+} E P_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z=(w+2\cdot m+3+5\cdot x+4\cdot y)/2$$

The crystalline AlPO-90 materials of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The AlPO-90 compositions of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and syngas shift process. Specific reaction conditions and the types of feeds which can be used in these processes are set forth in U.S. Pat. Nos. 4,310,440, 4,440,871 and 5,126,308, which are incorporated by reference.

The AlPO-90 materials may also be used as a catalyst for the conversion of methanol to olefins. The methanol can be in the liquid or vapor phase with the vapor phase being preferred. Contacting the methanol with the AlPO-90 catalyst can be done in a continuous mode or a batch mode with a continuous mode being preferred. The amount of time that the methanol is in contact with the AlPO-90 catalyst must be sufficient to convert the methanol to the desired light olefin products. When the process is carried out in a batch process, the contact time varies from about 0.001 hrs to about 1 hr and preferably from about 0.01 hr to about 1.0 hr. The longer contact times are used at lower temperatures while shorter times are used at higher temperatures. When the process is carried out in a continuous mode, the Weight Hourly Space Velocity (WHSV) based on methanol can vary from about 1 hr−1 to about 1000 hr−1 and preferably from about 1 hr−1 to about 100 hr−1.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 435° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e. g., methane, aromatic hydrocarbons, e. g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the AlPO-90 catalyst. When multiple reaction zones are used, one or more AlPO-90 catalysts may be used in series to produce the desired product mixture. Instead of a fixed bed, a dynamic bed system, (e. g., fluidized bed or moving bed), may be used. Such a dynamic system would facilitate any regeneration of the AlPO-90 catalyst that may be required. If regeneration is required, the AlPO-90 catalyst can be continuously introduced as a moving bed to a regeneration zone where it can be regenerated by means such as oxidation in an oxygen containing atmosphere to remove carbonaceous materials.

The AlPO-90 materials of this invention can also be used as an adsorbent for water vapor. The adsorbent may be a component of an adsorption heat pump apparatus. Adsorbents used for adsorption heat pump purposes are desired to have a high capacity for water vapor, as well as a large crystallographic density. The crystallographic density of microporous crystalline materials is conveniently expressed in units of T-atom/1000 Å³. Generally speaking, adsorbents with a low density can be problematic since they would require a large volume of material to take up a given quantity of adsorbate. This can be troublesome if space is limited in the application. It is thus of interest to consider uptake capacity on a volumetric basis as opposed to a gravimetric basis.

Any of the lines, conduits, units, devices, vessels, surrounding environments, zones or similar used in the process may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or received or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or received or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

By way of example, sensors and measurements as to a parameter of a conversion process comprising at least one reaction catalyzed by a calcined AlPO-90 that is thermally stable upon calcination, that can be characterized on an anhydrous basis by the empirical formula:

$$H_w M_m^{2+} E P_x Si_y O_z$$

where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, and "z" is the mole ratio of O to E and has a value determined by the equation:

$$z=(w+2\cdot m+3+5\cdot x+4\cdot y)/2$$

and may be characterized by the x-ray diffraction pattern, having at least the d-spacings and relative intensities set forth in Table 2 below:

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

Such sensors or measurements may be associated with any portion or component of the conversion process. Control of one or more conversion process parameters may be employed. The data sensed and received may be used as the basis for adjustment or control of a variety of parameters such as process variables and conditions. The data may provide predictive information.

Figure 4:
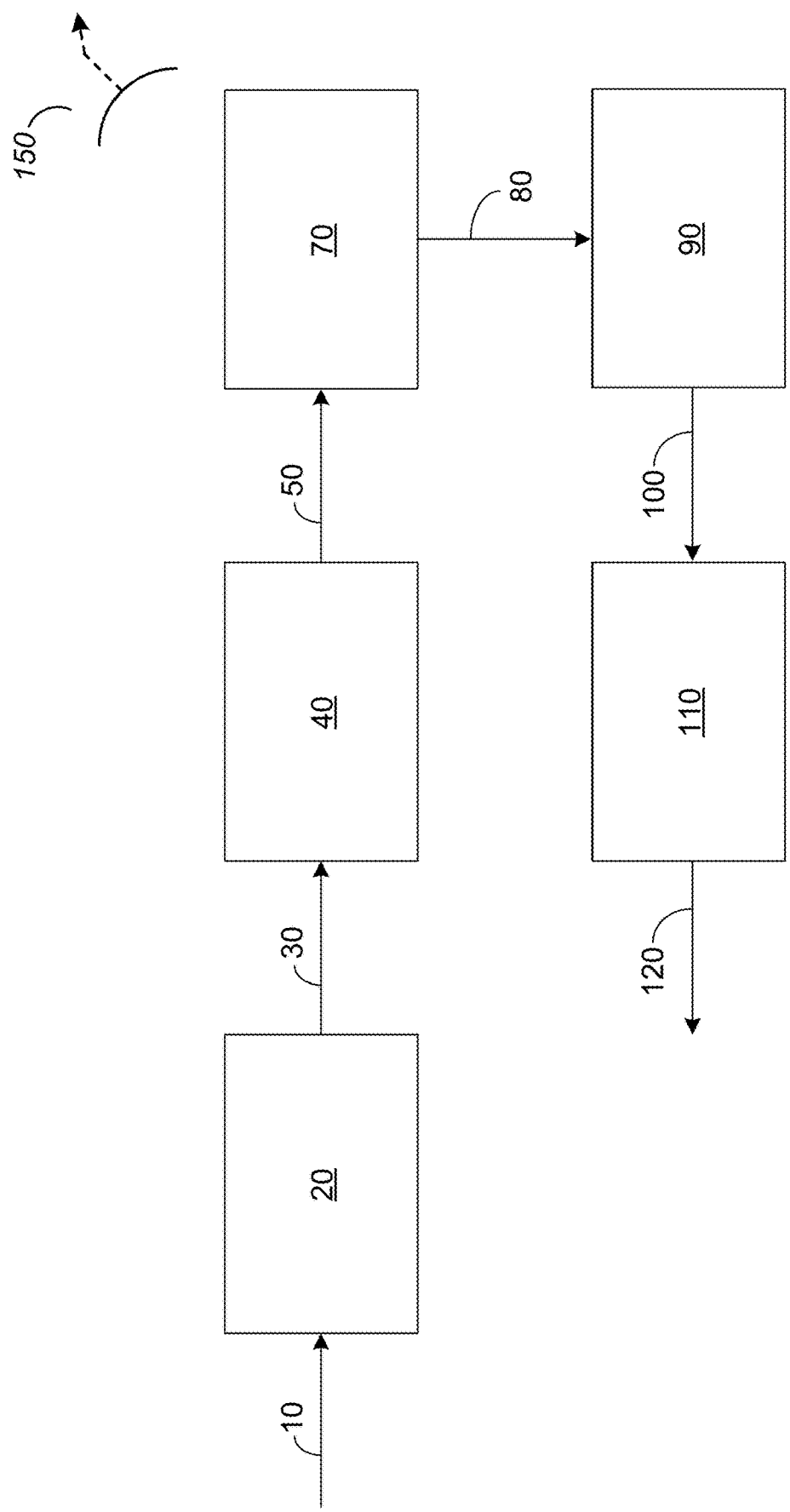
FIG. 4 illustrates a multi-unit, multi-stream, process having units and steams in fluid communication with, and downstream from or upstream to, a conversion process using as a catalyst, the microporous crystalline material AlPO-90 material in calcined form.

FIG. 4 illustrates a conversion process where a first feed in line 10 is introduced to a first unit 20 to provide a first effluent 30. The first effluent 30 in turn is introduced into second unit 40 to generate second effluent 50. Second effluent 50 is introduced to reactor 70 to contact the catalyst contained within reactor 70 and generate a reaction product. An effluent of the reactor is removed in line 80. Sensors, including analytical devices, may be employed anywhere reasonable in the conversion process equipment, as well as one or more transmitter(s), shown generally as 150. Examples of the data sensed may include process and levels monitoring, catalyst monitoring, asset health monitoring, safety applications, security monitoring and access, regulatory reporting and monitoring, asset location tracking, maintenance, turnaround activities, and the like. The data sensed may be of any streams or units in fluid communication and upstream or downstream of reactor 70, and or of reactor 70. The catalyst contained within reactor 70 is the catalyst described herein.

As will be appreciated by one of skill in the art upon reading the following disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more non-transitory computer-readable storage media having computer-readable program code, or instructions, embodied in or on the storage media. Any suitable computer-readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

Figure 5:
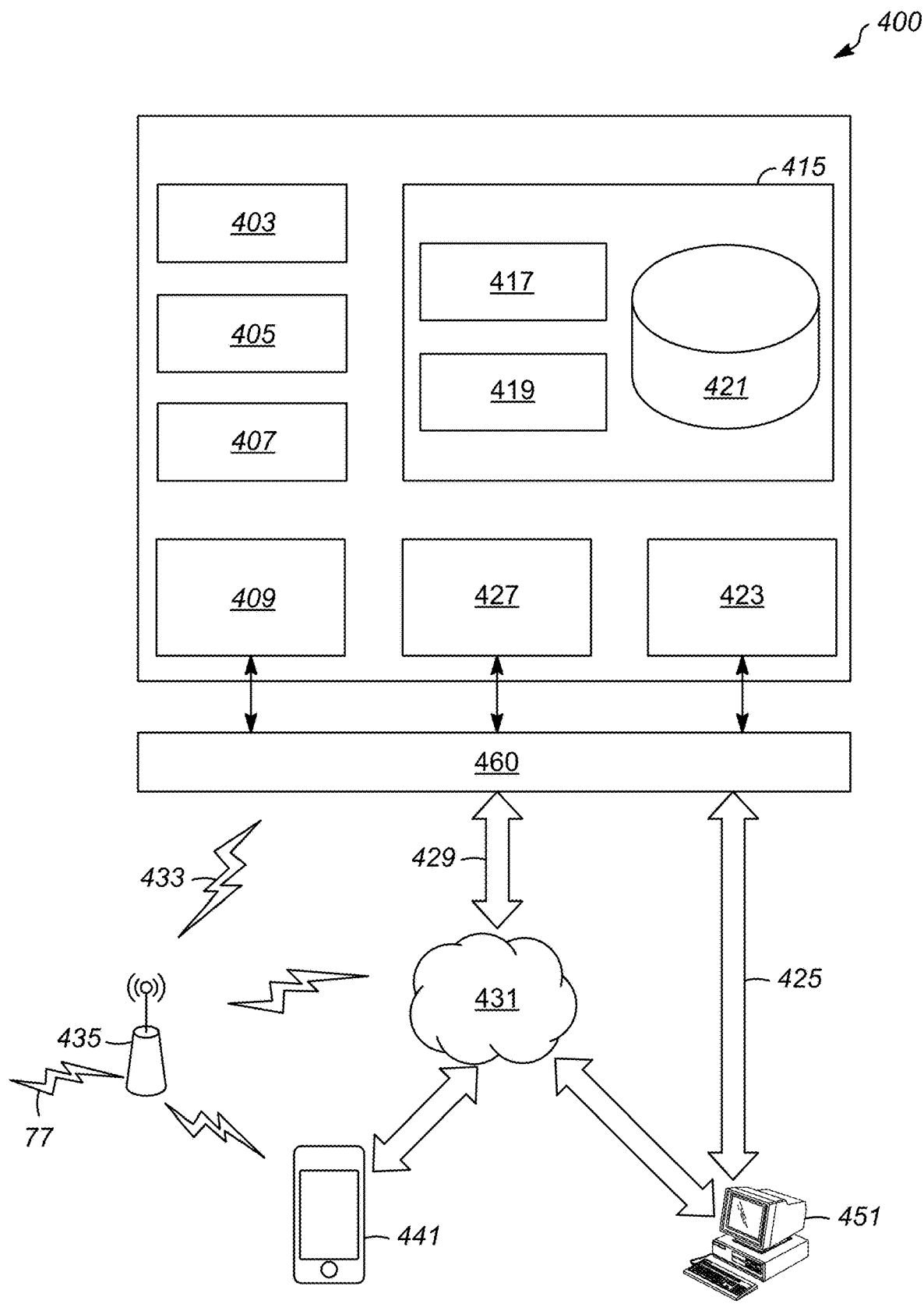
FIG. 5 shows a network environment and computing system that may be used to implement embodiments of the invention.

FIG. 5 illustrates a block diagram of a sensor data analysis system of the parameter data system 400 that may be used according to one or more illustrative embodiments of the disclosure. The parameter data system 400 may have a processor 403 for controlling overall operation of the parameter data system 400 and its associated components, including RAM 405, ROM 407, input/output module 409, and memory 415. The parameter data system 400, along with one or more additional devices (e.g., terminals 441, 451) may correspond to any of multiple systems or devices, such as mobile computing devices (e.g., smartphones, smart terminals, tablets, and the like) and/or refinery-based computing devices, configured as described herein for collecting and analyzing sensor data from devices associated with lines, vessels, or devices of one or more units, pertaining to operation or parameter of the one or more units.

Input/Output (I/O) 409 may include a microphone, keypad, touch screen, and/or stylus through which a user of the parameter data system 400 may provide input, and may also include one or more of a speaker for providing audio output and a video display device for providing textual, audiovisual and/or graphical output. Software may be stored within memory 415 and/or storage to provide instructions to processor 403 for enabling parameter data system 400 to perform various functions. For example, memory 415 may store software used by the parameter data system 400, such as an operating system 417, application programs 419, and an associated internal database 421. Processor 403 and its associated components may allow the parameter data system 400 to execute a series of computer-readable instructions to transmit or receive data, analyze data, and store analyzed data.

The parameter data system 400 may operate in a networked environment supporting connections to one or more remote computers, such as terminals/devices 441 and 451. Parameter data system 400, and related terminals/devices 441 and 451, may include devices or sensors associated with equipment, streams, or materials of a process employing streams and a reactor, including devices on-line or outside of equipment, streams, or materials, that are configured to receive and process data. Thus, the parameter data system 400 and terminals/devices 441 and 451 may each include personal computers (e.g., laptop, desktop, or tablet computers), servers (e.g., web servers, database servers), sensors, measurement devices, communication systems, or mobile communication devices (e.g., mobile phones, portable computing devices, and the like), and may include some or all of the elements described above with respect to the parameter data system 400.

Figure 3:
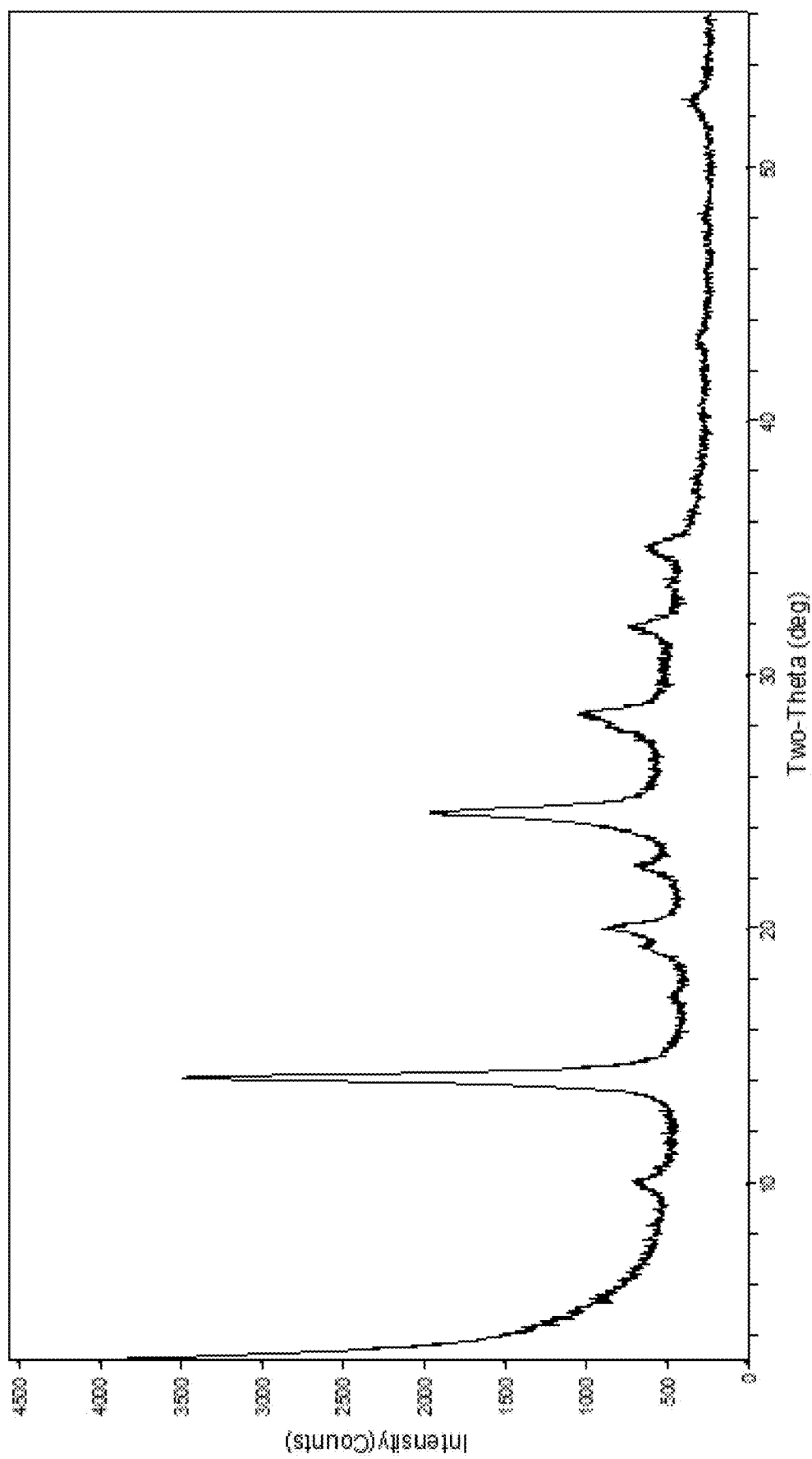
FIG. 3 is an x-ray diffraction pattern of an exemplary AlPO-90 material in the calcined form.

The network connections depicted in FIG. 5 include a local area network (LAN) 425 and a wide area network (WAN) 429, and a wireless telecommunications network 433, but may also include other networks. When used in a LAN networking environment, the parameter data system 400 may be connected to the LAN 425 through a network interface or adapter 423. When used in a WAN networking environment, the parameter data system 400 may include a modem 427 or other means for establishing communications over the WAN 429, such as network 431 (e.g., the Internet). When used in a wireless telecommunications network 433, the parameter data system 400 may include one or more transceivers, digital signal processors, and additional circuitry and software for communicating with wireless computing devices 441 (e.g., mobile phones, short-range communication systems, telematics devices) via one or more network devices 435 (e.g., base transceiver stations) in the wireless network 433. In one embodiment, any of the sensors and transmitters 150 may communicate with receiver 435 of parameter data system 400 of FIG. 3 via 77 which may be wired or wireless communication.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, Wi-Fi, and WiMAX, is presumed, and the various computing devices parameter data system components described herein may be configured to communicate using any of these network protocols or technologies.

Also, illustrated in FIG. 5 is a security and integration layer 460, through which communications may be sent and managed between the parameter data system 400 (e.g., a user's personal mobile device, a refinery-based system, external server, etc.) and the remote devices (441 and 451) and remote networks (425, 429, and 433). The security and integration layer 460 may comprise one or more separate computing devices, such as web servers, authentication servers, and/or various networking components (e.g., firewalls, routers, gateways, load balancers, etc.), having some or all of the elements described above with respect to parameter data system 400. As an example, a security and integration layer 460 of a mobile computing device, refinery-based device, or a server operated by a provider, an institution, governmental entity, or other organization, may comprise a set of web application servers configured to use secure protocols and to insulate the parameter data system 400 from external devices 441 and 451. In some cases, the security and integration layer 460 may correspond to a set of dedicated hardware and/or software operating at the same physical location and under the control of same entities as parameter data system 400. For example, layer 460 may correspond to one or more dedicated web servers and network hardware in an organizational datacenter or in a cloud infrastructure supporting a cloud-based parameter data system. In other examples, the security and integration layer 460 may correspond to separate hardware and software components which may be operated at a separate physical location and/or by a separate entity.

As discussed below, the data transferred to and from various devices of parameter data system 400 may include secure and sensitive data, such as measurement data, flow control data, concentration data, process parameter data, catalyst data, quantitative data, and instructions. In at least some examples, transmission of the data may be performed based on one or more user permissions provided. Therefore, it may be desirable to protect transmissions of such data by using secure network protocols and encryption, and also to protect the integrity of the data when stored in a database or other storage in a mobile device, analysis server, or other computing devices in the parameter data system 400, by using the security and integration layer 460 to authenticate users and restrict access to unknown or unauthorized users. In various implementations, security and integration layer 460 may provide, for example, a file-based integration scheme or a service-based integration scheme for transmitting data between the various devices in the parameter data system 400. Data may be transmitted through the security and integration layer 460, using various network communication protocols. Secure data transmission protocols and/or encryption may be used in file transfers to protect to integrity of the driving data, for example, File Transfer Protocol (FTP), Secure File Transfer Protocol (SFTP), and/or Pretty Good Privacy (PGP) encryption.

In other examples, one or more web services may be implemented within the parameter data system 400 and/or the security and integration layer 460. The web services may be accessed by authorized external devices and users to support input, extraction, and manipulation of the data (e.g., sensing data, concentration data, flow control data, etc.) between the parameter data system 400. Web services built to support the parameter data system 400 may be cross-domain and/or cross-platform, and may be built for enterprise use. Such web services may be developed in accordance with various web service standards, such as the Web Service Interoperability (WS-I) guidelines. In some examples, a flow control data and/or concentration data web service may be implemented in the security and integration layer 460 using the Secure Sockets Layer (SSL) or Transport Layer Security (TLS) protocol to provide secure connections between servers (e.g., the parameter data system 400) and various clients 441 and 451 (e.g., mobile devices, data analysis servers, etc.). SSL or TLS may use HTTP or HTTPS to provide authentication and confidentiality.

In other examples, such web services may be implemented using the WS-Security standard, which provides for secure SOAP messages using XML encryption. In still other examples, the security and integration layer 460 may include specialized hardware for providing secure web services. For example, secure network appliances in the security and integration layer 460 may include built-in features such as hardware-accelerated SSL and HTTPS, WS-Security, and firewalls. Such specialized hardware may be installed and configured in the security and integration layer 460 in front of the web servers, so that any external devices may communicate directly with the specialized hardware.

In some aspects, various elements within memory 415 or other components in parameter data system 400, may include one or more caches, for example, CPU caches used by the processing unit 403, page caches used by the operating system 417, disk caches of a hard drive, and/or database caches used to cache content from database 421. For embodiments including a CPU cache, the CPU cache may be used by one or more processors in the processing unit 403 to reduce memory latency and access time. In such examples, a processor 403 may retrieve data from or write data to the CPU cache rather than reading/writing to memory 415, which may improve the speed of these operations. In some examples, a database cache may be created in which certain data from a database 421 (e.g., an operating parameter database, a concentration database, correlation database, etc.) is cached in a separate smaller database on an application server separate from the database server. For instance, in a multi-tiered application, a database cache on an application server can reduce data retrieval and data manipulation time by not needing to communicate over a network with a back-end database server. These types of caches and others may be included in various embodiments, and may provide potential advantages in certain implementations of retrieving data, collecting data, receiving data, recording data, processing data, and analyzing data, such as faster response times and less dependence on network conditions when transmitting/receiving data.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, Wi-Fi, and WiMAX, is presumed, and the various computer devices and system components described herein may be configured to communicate using any of these network protocols or technologies.

Additionally, one or more application programs 419 may be used by the parameter data system 400 (e.g., process software applications, device configuration software applications, control software applications, and the like), including computer executable instructions for receiving and storing data from refinery-based systems, and/or mobile computing devices, determining and configuring the mobile computing device based on the retrieved and analyzed data, and/or performing other related functions as described herein.

The following examples are presented in illustration of this invention and are not intended as undue limitations on the generally broad scope of the invention as set out in the appended claims. The products will be designated with names that contain the suffix "–90" to indicate the "–90" structure and prefix that reflects the compositional nature of the product, such as "SAPO" for a silicoaluminophosphate, "ZnAPO" for a zinc aluminophosphate, and "MgAPSO" for a magnesium silicoaluminophosphate, etc.

The structure of the AlPO-90 compositions of this invention was determined by x-ray analysis. The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_0$," being the intensity of the strongest line or peak, and "I" being the intensity of each of the other peaks.

As will be understood by those skilled in the art, the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, w, and vw which represent very strong, strong, medium, weak, and very weak respectively. In terms of $100 \times I/I_0$, the above designations are defined as:

vw=0-5; w=5-15; m=15-40: s=40-75 and vs=75-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

468.1 g of water was added to a three-necked 2-liter round bottom flask equipped with a condenser, overhead mixer, thermocouple, and a nitrogen blanket over the top of the condenser. The flask was placed in an ice bath. 261.7 g of 1,4-dibromobutane (99%) was added to the flask. The temperature of the mixture reached 8° C. before 206.4 g of piperidine (99%) was slowly added. The temperature of the mixture was 29° C. after addition of the piperidine, then steadily rose to a peak temperature of 70° C. Once the temperature started dropping from its peak, the cloudy white mixture became clear, and was mixed for an additional 2 hours.

Example 2

885 g of the product from Example 1 was added to a three-necked 2 liter round bottom flask equipped with an overhead mixer. 283.9 g of $Ag_2O$ was added to the flask and stirred at room temperature for 1 day. The mixture is grey in color. The mixture was then filtered to remove precipitated silver bromide. The remaining mixture was then analyzed for water content, which showed it was 70.5% water.

Example 3

20.11 g of the product from Example 2 was combined with 2.37 g of tetramethylammonium hydroxide (TMAOH; Sigma-Aldrich, 25%). 1.94 g of $Al(OH)_3$ (Pfaltz & Bauer) was then added to the mixture followed by 0.22 g of Ludox AS-40 (Sigma-Aldrich, 40% $SiO_2$). 5.36 g of phosphoric acid (Fisher; 85%) was then slowly added. The material was then mixed for 30 minutes. The mixture was then transferred to a 45 cc autoclave and held at 170° C. in a tumble oven for 3 days. After cooling to room temperature, the material was isolated via centrifugation and dried at 100° C. overnight. ICP analysis showed a composition of 1.70% Si, 21.2% Al, 24.6% P (weight percent). CHN analysis showed 12.6% C, 2.89% H, 2.45% N (weight percent). XRD analysis of the material gave the following peaks:

| 2-Theta | d(Å) | Intensity |
|---|---|---|
| 9.8883 | 8.9377 | w |
| 13.9716 | 6.3334 | m |
| 17.2166 | 5.1463 | vw |
| 18.7904 | 4.7187 | w |
| 19.7852 | 4.4836 | s |
| 22.1931 | 4.0023 | w |
| 23.5708 | 3.7714 | w |
| 24.3648 | 3.6503 | vs |
| 27.5523 | 3.2348 | w |
| 28.1685 | 3.1654 | m |
| 31.5141 | 2.8366 | m |
| 33.2654 | 2.6911 | vw |
| 34.6595 | 2.586 | w |
| 40.246 | 2.239 | vw |
| 42.9014 | 2.1064 | w |
| 47.7024 | 1.905 | w |
| 51.9222 | 1.7596 | m |

This material was determined to be SAPO-90 by XRD.

Example 4

20.26 g of the product from Example 2 was combined with 2.39 g of tetramethylammonium hydroxide (TMAOH; Sigma-Aldrich, 25%). 1.96 g of Al(OH)$_3$ (Pfaltz & Bauer) was then added to the mixture followed by 5.4 g of phosphoric acid (Fisher; 85%) slowly. The material was mixed for 30 minutes. The mixture was then transferred to a 45 cc autoclave and held at 160° C. in a tumble oven for 2 days. After cooling to room temperature, the material was isolated via centrifugation and dried at 100° C. overnight. XRD analysis of the material gave the following peaks:

| 2-Theta | d(Å) | Intensity |
|---|---|---|
| 9.9092 | 8.9189 | m |
| 14.0904 | 6.2803 | m |
| 17.2562 | 5.1346 | w |
| 18.9086 | 4.6895 | vw |
| 19.8646 | 4.4659 | m |
| 22.3234 | 3.9792 | m |
| 23.6282 | 3.7624 | w |
| 24.4941 | 3.6313 | vs |
| 27.6099 | 3.2282 | m |
| 28.3668 | 3.1437 | m |
| 31.6819 | 2.8219 | w |
| 33.3349 | 2.6857 | vw |
| 34.3206 | 2.6108 | w |
| 34.8282 | 2.5739 | w |
| 42.6232 | 2.1195 | vw |
| 43.1211 | 2.0961 | w |
| 47.8905 | 1.8979 | vw |
| 52.3698 | 1.7456 | w |

The product was determined to be AlPO-90 by XRD.

Example 5

20.26 g of the product from Example 2 was combined with 2.39 g of tetramethylammonium hydroxide (TMAOH; Sigma-Aldrich, 25%). 1.96 g of Al(OH)$_3$ (Pfaltz & Bauer) was then added to the mixture followed by 5.4 g of phosphoric acid (Fisher; 85%) slowly. The material was mixed for 30 minutes. The mixture was then transferred to a 45 cc autoclave and held at 170° C. in a tumble oven for 2 days. After cooling to room temperature, the material was isolated via centrifugation and dried at 100° C. overnight. XRD analysis of the material gave the following peaks:

| 2-Theta | d(Å) | Intensity |
|---|---|---|
| 9.8694 | 8.9548 | m |
| 14.0805 | 6.2847 | m |
| 17.2366 | 5.1404 | w |
| 18.8794 | 4.6966 | w |
| 19.8548 | 4.4681 | m |
| 22.2939 | 3.9844 | m |
| 23.6083 | 3.7655 | w |
| 24.4742 | 3.6342 | vs |
| 27.6004 | 3.2293 | m |
| 28.3469 | 3.1459 | m |
| 31.6522 | 2.8245 | w |
| 33.3643 | 2.6834 | vw |
| 34.3506 | 2.6086 | w |
| 34.8576 | 2.5718 | w |
| 42.5946 | 2.1208 | vw |
| 43.0913 | 2.0975 | w |
| 47.82 | 1.9005 | vw |
| 52.3299 | 1.7469 | w |

The product was determined to be AlPO-90 by XRD.

Example 6

13.34 g of water was combined with 93.89 g of the product from Example 1 followed by 12.66 g of tetramethylammonium hydroxide (TMAOH; Sigma-Aldrich, 25%). 10.37 g of Al(OH)$_3$ (Pfaltz & Bauer) was then added to the mixture followed by 1.17 g of Ludox AS-40 (Sigma-Aldrich, 40% SiO$_2$) and 28.60 g of phosphoric acid (Fisher; 85%) slowly. The material was mixed for 30 minutes. The mixture was then transferred to a 300 cc stirred autoclave and held at 170° C. for 2 days with a stir rate of 300 rpm. After cooling to room temperature, the material was isolated via centrifugation and dried at 100° C. overnight. ICP analysis showed a composition of 1.66% Si, 20.7% Al, 25.4% P (weight percent). XRD analysis of the material gave the following peaks:

| 2-Theta | d(Å) | Intensity |
|---|---|---|
| 9.8692 | 8.955 | w |
| 14.0209 | 6.3113 | m |
| 17.2355 | 5.1407 | vw |
| 19.8051 | 4.4792 | m |
| 22.1942 | 4.0021 | w |
| 24.3648 | 3.6503 | vs |
| 27.561 | 3.2338 | w |
| 28.2375 | 3.1578 | m |
| 31.6023 | 2.8289 | w |
| 33.2637 | 2.6913 | vw |
| 34.6887 | 2.5839 | m |
| 40.2936 | 2.2365 | vw |
| 42.7826 | 2.1119 | w |
| 47.7112 | 1.9046 | vw |
| 52.0912 | 1.7543 | w |

The product was determined to be SAPO-90 by XRD.

Example 7

The product from Example 3 was calcined in air at 600° C. for 4 hours in a muffle furnace. The temperature was ramped up to 600° C. at a rate of 2° C./min. The material was then cooled to room temperature. XRD analysis of the material gave the following peaks:

| 2-Theta | d(Å) | Intensity |
|---|---|---|
| 10.0499 | 8.7944 | w |
| 14.1305 | 6.2626 | vs |
| 19.2316 | 4.6114 | vw |
| 20.0628 | 4.4222 | w |
| 22.4897 | 3.9502 | vw |
| 24.5834 | 3.6183 | s |
| 27.8886 | 3.1965 | w |
| 28.3884 | 3.1414 | m |
| 31.8925 | 2.8038 | w |
| 35.0573 | 2.5576 | w |
| 52.6388 | 1.7373 | vw |

The calcined SAPO-90 product was pressed into a pellet and loaded in a McBain gravimetric balance for adsorption studies. It was observed that the SAPO-90 took up 14.3% water by weight and 3.0% n-butane by weight.

Example 8

The product from Example 4 was calcined in air at 650° C. for 8 hours in a muffle furnace. The temperature was ramped up to 650° C. at a rate of 1-2° C./min. The material was then cooled to room temperature. XRD analysis of the material gave the following peaks:

| 2-Theta | d(Å) | Intensity |
|---|---|---|
| 10.0089 | 8.8303 | w |
| 14.1602 | 6.2495 | vs |
| 17.2659 | 5.1317 | vw |
| 19.3174 | 4.5911 | m |
| 20.0739 | 4.4198 | m |
| 22.4733 | 3.953 | m |
| 24.0265 | 3.7009 | m |
| 24.6434 | 3.6096 | vs |
| 27.9788 | 3.1864 | m |
| 28.5356 | 3.1255 | m |
| 31.9707 | 2.7971 | w |
| 33.6032 | 2.6648 | vw |
| 35.1167 | 2.5534 | w |
| 52.8083 | 1.7322 | vw |

Example 9

The product from Example 5 was calcined in air at 650° C. for 8 hours in a muffle furnace. The temperature was ramped up to 650° C. at a rate of 1-2° C./min. The material was then cooled to room temperature. XRD analysis of the material gave the following peaks:

| 2-Theta | d(Å) | Intensity |
|---|---|---|
| 9.9987 | 8.8393 | w |
| 14.1601 | 6.2495 | vs |
| 17.3757 | 5.0996 | vw |
| 19.3271 | 4.5888 | m |
| 20.0938 | 4.4155 | m |
| 22.4628 | 3.9548 | w |
| 24.0262 | 3.7009 | m |
| 24.6534 | 3.6082 | s |
| 27.9588 | 3.1887 | m |
| 28.5061 | 3.1287 | m |
| 31.9908 | 2.7954 | w |
| 33.5239 | 2.671 | vw |
| 35.1566 | 2.5506 | w |
| 52.8279 | 1.7316 | vw |

Example 10

The product from Example 6 was calcined in air at 650° C. for 8 hours in a muffle furnace. The temperature was ramped up to 650° C. at a rate of 1-2° C./min. The material was then cooled to room temperature. XRD analysis of the material gave the following peaks:

| 2-Theta | d(Å) | Intensity |
|---|---|---|
| 9.9696 | 8.865 | w |
| 14.1502 | 6.2539 | vs |
| 20.0939 | 4.4154 | w |
| 22.4128 | 3.9636 | vw |
| 24.6037 | 3.6154 | s |
| 27.9481 | 3.1899 | w |
| 28.4562 | 3.134 | m |
| 31.9111 | 2.8022 | w |
| 35.0572 | 2.5576 | w |
| 52.6095 | 1.7382 | vw |

Comparative Example 1

9.49 g of water was combined with 12.58 g of tetramethylammonium hydroxide (TMAOH; Sigma-Aldrich, 25%). 2.07 g of Al(OH)$_3$ (Pfaltz & Bauer) was then added to the mixture followed 0.25 g of Ludox AS-40 (Sigma-Aldrich, 40% SiO$_2$). 5.70 g of phosphoric acid (Fisher; 85%) was then slowly added. The material was mixed for 30 minutes. The mixture was then transferred to a 45 cc autoclave and held at 170° C. in a tumble oven for 3 days. After cooling to room temperature, the material was isolated via centrifugation and dried at 100° C. overnight. XRD analysis of the material showed that it was AlPO-20 (SOD structure).

Specific Embodiments

While the following is described in conjunction with specific embodiments, it will be understood that this description is intended to illustrate and not limit the scope of the preceding description and the appended claims.

A first embodiment of the invention is a microporous crystalline material that has an empirical composition in an as-synthesized form and on an anhydrous basis expressed by an empirical formula $C^+_c A^+_a M_m^{2+} EP_x Si_y O_z$ where M is at least one framework divalent cation and is selected from the group consisting of alkaline earth and transition metals, wherein M is a cation selected from the group consisting of beryllium, magnesium, cobalt (II), manganese, zinc, iron (II), nickel and mixtures thereof, C is a cyclic organoammonium cation, A is an acyclic organoammonium cation, the ratio (c/a) having a value from 0.01 to about 100, and the sum (c+a) representing the mole ratio of (C+A) to E and has a value of about 0.1 to about 2.0, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron(III) and boron and "z" is a mole ratio of O to E and is given by an equation $z=(2 \cdot m+c+a+3 \cdot 5 \cdot x+4 \cdot y)/2$ and is characterized by a following x-ray diffraction pattern, having at least the d-spacings and relative intensities set forth in Table 1.

TABLE 1

| 2-theta(°) | d (Å) | Intensity |
|---|---|---|
| 9.86-9.91 | 8.96-8.91 | w-m |
| 13.97-14.10 | 6.34-6.28 | m |
| 17.21-17.26 | 5.15-5.13 | vw-w |
| 18.79-18.91 | 4.72-4.68 | vw-w |
| 19.78-19.87 | 4.49-4.46 | m-s |
| 22.19-22.33 | 4.01-3.97 | w-m |
| 23.57-23.63 | 3.78-3.76 | w |
| 24.36-24.50 | 3.66-3.63 | vs |
| 27.55-27.61 | 3.24-3.22 | w-m |
| 28.16-28.37 | 3.17-3.14 | m |
| 31.51-31.69 | 2.84-2.82 | w-m |
| 33.26-33.37 | 2.70-2.68 | vw |
| 34.32-34.86 | 2.62-2.57 | w-m |
| 42.59-42.91 | 2.13-2.10 | vw-w |
| 47.70-47.90 | 1.91-1.89 | vw-w |
| 51.92-52.37 | 1.76-1.74 | w-m |

An embodiment of the invention is one, any or all of prior embodiments in this paragraph up through the first embodiment in this paragraph wherein after being calcined the AlPO-90 material is characterized by the x-ray diffraction pattern, having at least the d-spacings and relative intensities set forth in Table 2 below.

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

An embodiment of the invention is one, any or all of prior embodiments in this paragraph up through the first embodiment in this paragraph wherein the AlPO-90 material is characterized on an anhydrous basis by the empirical formula $H_w M_m^{2+} E P_x Si_y O_z$ where M is at least one metal cation of valence +2 selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, "w" is the mole ratio of H to E and varies from 0 to 2.5, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0.05 to about 1.0, "m"+"y"≥0.1, and "z" is the mole ratio of O to E and has a value determined by the equation $z=(w+2 \cdot m+3+5 \cdot x+4 \cdot y)/2$. An embodiment of the invention is one, any or all of prior embodiments in this paragraph up through the first embodiment in this paragraph wherein the microporous crystalline material indexes on a unit cell with hexagonal axes with lattice parameters a=12.768 Å and c=15.333 Å and has an ABC-6 net structure with the stacking sequence repeating every 6 layers along the c-axis (p=15.333/2.5=6.13). An embodiment of the invention is one, any or all of prior embodiments in this paragraph up through the first embodiment in this paragraph wherein the microporous crystalline material can be described as a combination of two zeotypes with stacking sequences of AABCBC and ABACBC. An embodiment of the invention is one, any or all of prior embodiments in this paragraph up through the first embodiment in this paragraph wherein the microporous crystalline material has a percentage of AABCBC zeotype that can be defined as x and the percentage of ABACBC zeotype can be defined as (100−x), where x ranges from 0-100, inclusive.

A second embodiment of the invention is a method of making a AlPO-90 microporous crystalline material comprising preparing a reaction mixture containing reactive sources described in terms of molar ratios of the oxides by a formula $aA_2O\ bC_2O\ cMO\ E_2O_3\ dP_2O_5\ eSiO_2\ fH_2O$ where "a" has a value of about 0.01 to about 5, "b" has a value of about 0.01 to about 5, "c" has a value of about 0 to about 2, "d" has a value of about 0.5 to about 8, "e" has a value of about 0 to about 4, and "f" has a value from 30 to 1000, wherein reactive sources of C, A, E, phosphorus and one or both M and silicon; reacting the reaction mixture at a temperature from about 60° C. to about 200° C. for a period of about 1 day to about 21 days; and isolating a solid product from a heterogeneous mixture wherein the AlPO-90 microporous material, is characterized by the x-ray following diffraction pattern, having at least the d-spacings and relative intensities set forth in Table 1:

TABLE 1

| 2-theta(°) | d (Å) | Intensity |
|---|---|---|
| 9.86-9.91 | 8.96-8.91 | w-m |
| 13.97-14.10 | 6.34-6.28 | m |
| 17.21-17.26 | 5.15-5.13 | vw-w |
| 18.79-18.91 | 4.72-4.68 | vw-w |
| 19.78-19.87 | 4.49-4.46 | m-s |
| 22.19-22.33 | 4.01-3.97 | w-m |
| 23.57-23.63 | 3.78-3.76 | w |
| 24.36-24.50 | 3.66-3.63 | vs |
| 27.55-27.61 | 3.24-3.22 | w-m |
| 28.16-28.37 | 3.17-3.14 | m |
| 31.51-31.69 | 2.84-2.82 | w-m |
| 33.26-33.37 | 2.70-2.68 | vw |
| 34.32-34.86 | 2.62-2.57 | w-m |
| 42.59-42.91 | 2.13-2.10 | vw-w |
| 47.70-47.90 | 1.91-1.89 | vw-w |
| 51.92-52.37 | 1.76-1.74 | w-m |

An embodiment of the invention is one, any or all of prior embodiments in this paragraph up through the first embodiment in this paragraph wherein the AlPO-90 is calcined at a temperature of at least 550° C. and is characterized by the x-ray diffraction pattern, having at least the d-spacings and relative intensities set forth in Table 2 below:

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

An embodiment of the invention is one, any or all of prior embodiments in this paragraph up through the first embodiment in this paragraph wherein the sources of aluminum are selected from the group consisting of aluminum alkoxides, precipitated aluminas, aluminum metal, aluminum hydroxide, aluminum salts and alumina sols. An embodiment of the invention is one, any or all of prior embodiments in this paragraph up through the first embodiment in this paragraph wherein sources of phosphorus are selected from the group consisting of orthophosphoric acid, phosphorus pentoxide, and ammonium dihydrogen phosphate. An embodiment of the invention is one, any or all of prior embodiments in this paragraph up through the first embodiment in this paragraph wherein sources of silica are selected from the group consisting of tetraethylorthosilicate, colloidal silica, and precipitated silica. An embodiment of the invention is one, any or all of prior embodiments in this paragraph up through the first embodiment in this paragraph wherein sources of E elements are selected from the group consisting of organoammonium borates, boric acid, precipitated gallium oxyhydroxide, gallium sulfate, ferric sulfate, and ferric chloride. An embodiment of the invention is one, any or all of prior embodiments in this paragraph up through the first embodiment in this paragraph wherein sources of the M metals are selected from the group consisting of halide salts, nitrate salts, acetate salts, and sulfate salts of the respective alkaline earth and transition metals. An embodiment of the invention is one, any or all of prior embodiments in this paragraph up through the first embodiment in this paragraph wherein C is an organoammonium cation prepared from a reaction of an aqueous mixture of a cyclic secondary amine and an organic dihalide. An embodiment of the invention is one, any or all of prior embodiments in this paragraph up through the first embodiment in this paragraph wherein the cyclic secondary amines are selected from the group consisting of piperidine, homopiperidine, pyrrolidine, and morpholine. An embodiment of the invention is one, any or all of prior embodiments in this paragraph up through the first embodiment in this paragraph wherein A is an acyclic organoammonium cation represented as $NR_4^+$. An embodiment of the invention is one, any or all of prior embodiments in this paragraph up through the first embodiment in this paragraph wherein the R groups are, independently, aliphatic carbon chains of the formula $C_nH_{2n+1}$, where n is a whole number ranging from 1 to 4, inclusive. An embodiment of the invention is one, any or all of prior embodiments in this paragraph up through the first embodiment in this paragraph wherein the AlPO-90 microporous crystalline material is calcined at a temperature of at least 600° C. An embodiment of the invention is one, any or all of prior embodiments in this paragraph up through the first embodiment in this paragraph wherein the AlPO-90 microporous crystalline material is calcined at a temperature of at least 650° C.

A third embodiment of the invention is a process of separating mixtures of molecular species, removing contaminants or catalyzing hydrocarbon conversion processes comprising contacting a feed stream with a microporous crystalline material that has an empirical composition in a calcined form and on an anhydrous basis expressed by an empirical formula $H_wM_m^{2+}EP_xSi_yO_z$ where M is at least one framework divalent cation and is selected from the group consisting of alkaline earth and transition metals, wherein M is a cation selected from the group consisting of beryllium, magnesium, cobalt (II), manganese, zinc, iron(II), nickel and mixtures thereof. H is a proton, w" is the mole ratio of H to E and varies from 0 to 2.5, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron(III) and boron and "z" is a mole ratio of O to E and is given by an equation $z=(2 \cdot m + r + 3 + 5 \cdot x + 4 \cdot y)/2$ and is characterized by an x-ray following diffraction pattern, having at least the d-spacings and relative intensities set forth in Table 2

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

An embodiment of the invention is one, any or all of prior embodiments in this paragraph up through the second embodiment in this paragraph wherein the separation of molecular species is in an operation of an adsorption heat pump wherein water vapor is adsorbed by the microporous crystalline material. An embodiment of the invention is one, any or all of prior embodiments in this paragraph up through the second embodiment in this paragraph wherein the hydrocarbon conversion processes are selected from the group consisting of cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and a syngas shift process. An embodiment of the invention is one, any or all of prior embodiments in this paragraph up through the second embodiment in this paragraph wherein the separation of molecular species is based on the molecular size (kinetic diameter) or on the degree of polarity of the molecular species.

A fourth embodiment of the invention is a system comprising (a) at least one processor; (b) at least one memory storing computer-executable instructions; and (c) at least one receiver configured to receive data of a parameter of at least one unit or stream in fluid communication with and downstream from or upstream to a conversion process of separating mixtures of molecular species, removing contaminants or catalyzing hydrocarbon conversion processes comprising contacting a feed stream with a microporous crystalline material that has an empirical composition in a calcined form and on an anhydrous basis expressed by an empirical formula $H_wM_m^{2+}EP_xSi_yO_z$ where M is at least one framework divalent cation and is selected from the group consisting of alkaline earth and transition metals, wherein M is a cation selected from the group consisting of beryllium, magnesium, cobalt (II), manganese, zinc, iron(II), nickel and mixtures thereof. H is a proton, w" is the mole ratio of H to E and varies from 0 to 2.5, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron(III) and boron and "z" is a mole ratio of O to E and is given by an equation $z=(2 \cdot m + r + 3 + 5 \cdot x + 4 \cdot y)/2$ and is characterized by an x-ray following diffraction pattern, having at least the d-spacings and relative intensities set forth in Table 2

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

An embodiment of the invention is one, any or all of prior embodiments in this paragraph up through the first embodiment in this paragraph wherein the hydrocarbon conversion processes are selected from the group consisting of cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and a syngas shift process An embodiment of the invention is one, any or all of prior embodiments in this paragraph up through the first embodiment in this paragraph wherein the separation of molecular species is in an operation of an adsorption heat pump wherein water vapor is adsorbed by the microporous crystalline material. An embodiment of the invention is one, any or all of prior embodiments in this paragraph up through the first embodiment in this paragraph wherein the at least one unit or stream is not in direct fluid communication with the conversion process. An embodiment of the invention is one, any or all of prior embodiments in this paragraph up through the first embodiment in this paragraph further comprising an Input/Output device to collect the data. An embodiment of the invention is one, any or all of prior embodiments in this paragraph up through the first embodiment in this paragraph wherein the processor is configured to evaluate the data. An embodiment of the invention is one, any or all of prior embodiments in this paragraph up through the first embodiment in this paragraph wherein the processor is configured to correlate the data. An embodiment of the invention is one, any or all of prior embodiments in this paragraph up through the first embodiment in this paragraph further comprising a transmitter to transmit a signal to the conversion process. An embodiment of the invention is one, any or all of prior embodiments in this paragraph up through the first embodiment in this paragraph wherein the signal comprises instructions. An embodiment of the invention is one, any or all of prior embodiments in this paragraph up through the first embodiment in this paragraph wherein the signal comprises instructions regarding an adjustment to a parameter. An embodiment of the invention is one, any or all of prior embodiments in this paragraph up through the first embodiment in this paragraph further comprising collecting data from multiple systems wherein one system is the parameter data.

A fifth embodiment of the invention is a system. An embodiment of the invention is one, any or all of prior embodiments in this paragraph up through the second embodiment in this paragraph wherein the processor is configured to generate predictive information. An embodiment of the invention is one, any or all of prior embodiments in this paragraph up through the second embodiment in this paragraph wherein the processor is configured to generate quantitative information.

A sixth embodiment of the invention is a method for collecting data from a conversion process, the method comprising receiving data from at least one sensor of least one unit or stream in fluid communication with and downstream from or upstream to a conversion process, the conversion process comprising at least one reaction catalyzed by a microporous crystalline material that has an empirical composition in a calcined form and on an anhydrous basis expressed by an empirical formula $H_w M_m^{2+} EP_x Si_y O_z$ where M is at least one framework divalent cation and is selected from the group consisting of alkaline earth and transition metals, wherein M is a cation selected from the group consisting of beryllium, magnesium, cobalt (II), manganese, zinc, iron(II), nickel and mixtures thereof. H is a proton, "w" is the mole ratio of H to E and varies from 0 to 2.5, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron(III) and boron and "z" is a mole ratio of O to E and is given by an equation $z=(2 \cdot m+r+3+5 \cdot x+4 \cdot y)/2$ and is characterized by an x-ray following diffraction pattern, having at least the d-spacings and relative intensities set forth in Table 2

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw |

An embodiment of the invention is one, any or all of prior embodiments in this paragraph up through the sixth embodiment in this paragraph further comprising at least one of displaying or transmitting or analyzing the received data. An embodiment of the invention is one, any or all of prior embodiments in this paragraph up through the sixth embodiment in this paragraph further comprising analyzing the received data to generate at least one instruction and transmitting the at least one instruction. An embodiment of the invention is one, any or all of prior embodiments in this paragraph up through the sixth embodiment in this paragraph further comprising analyzing the received data and generating predictive information. An embodiment of the invention is one, any or all of prior embodiments in this paragraph up through the sixth embodiment in this paragraph further comprising analyzing the received data and generating quantitative information. An embodiment of the invention is one, any or all of prior embodiments in this paragraph up through the third embodiment in this paragraph wherein the at least one unit or stream is not in direct fluid communication with the conversion process.

The invention claimed is:
1. A parameter data system comprising:
(a) at least one processor;
(b) at least one memory storing non-transitory computer-executable instructions; and

(c) at least one receiver configured to receive data of a parameter of at least one unit or stream in fluid communication with and downstream from or upstream to a conversion process of separating mixtures of molecular species, removing contaminants or catalyzing hydrocarbon conversion processes comprising contacting a feed stream with a microporous crystalline material that has an empirical composition in a calcined form and on an anhydrous basis expressed by an empirical formula:

$$H_w M_m^{2+} EP_x Si_y O_z$$

where M is at least one framework divalent cation and is selected from the group consisting of alkaline earth and transition metals, H is a proton, "w" is the mole ratio of H to E and varies from 0 to 2.5, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron(III) and boron and "z" is a mole ratio of O to E and is given by an equation:

$$z = (2 \cdot m + r + 3 + 5 \cdot x + 4 \cdot y)/2$$

and is characterized by an x-ray following diffraction pattern, having at least the d-spacings and relative intensities set forth in Table 2:

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw. |

2. The system of claim 1 wherein said hydrocarbon conversion processes are selected from the group consisting of cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and a syngas shift process.

3. The system of claim 1 wherein the separation of molecular species is in an operation of an adsorption heat pump wherein water vapor is adsorbed by said microporous crystalline material.

4. The process of claim 1 wherein the at least one unit or stream is not in direct fluid communication with the conversion process.

5. The system of claim 1 further comprising an Input/Output device to collect the data.

6. The system of claim 1 wherein the processor is configured to evaluate the data.

7. The system of claim 1 wherein the processor is configured to correlate the data.

8. The system of claim 1 further comprising a transmitter to transmit a signal to the conversion process.

9. The system of claim 8 wherein the signal comprises instructions.

10. The system of claim 9 wherein the signal comprises instructions regarding an adjustment to a parameter.

11. The system of claim 1 further comprising collecting data from multiple systems wherein one system is the parameter data system.

12. The system of claim 1 wherein the processor is configured to generate predictive information.

13. The system of claim 1 wherein the processor is configured to generate quantitative information.

14. A method for collecting data from a conversion process, the method comprising receiving data of a parameter from at least one sensor of at least one unit or stream in fluid communication with and downstream from or upstream to a conversion process, the conversion process comprising at least one reaction catalyzed by a microporous crystalline material that has an empirical composition in a calcined form and on an anhydrous basis expressed by an empirical formula:

$$H_w M_m^{2+} EP_x Si_y O_z$$

where M is at least one framework divalent cation and is selected from the group consisting of alkaline earth and transition metals, H is a proton, "w" is the mole ratio of H to E and varies from 0 to 2.5, "m" is the mole ratio of M to E and varies from 0 to about 1.0, "x" is a mole ratio of P to E and varies from 0.5 to about 2.0, a ratio of silicon to E is represented by "y" which varies from about 0 to about 1.0, E is a trivalent element which is tetrahedrally coordinated, is present in the framework, and is selected from the group consisting of aluminum, gallium, iron(III) and boron and "z" is a mole ratio of O to E and is given by an equation:

$$z = (2 \cdot m + r + 3 + 5 \cdot x + 4 \cdot y)/2$$

and is characterized by an x-ray following diffraction pattern, having at least the d-spacings and relative intensities set forth in Table 2:

TABLE 2

| 2-theta(°) | d (Å) | Intensity |
|---|---|---|
| 9.96-10.05 | 8.87-8.79 | w |
| 14.13-14.17 | 6.27-6.24 | vs |
| 19.23-19.32 | 4.62-4.59 | vw-m |
| 20.06-20.10 | 4.43-4.41 | w-m |
| 22.41-22.49 | 3.97-3.95 | vw-m |
| 24.02-24.65 | 3.71-3.60 | m-vs |
| 27.88-27.98 | 3.20-3.18 | w-m |
| 28.38-28.54 | 3.15-3.12 | m |
| 31.89-31.98 | 2.81-2.79 | w |
| 35.05-35.12 | 2.56-2.55 | w |
| 52.60-52.81 | 1.74-1.73 | vw. |

15. The method of claim 14 further comprising at least one of displaying or transmitting or analyzing the received data.

16. The method of claim 14 further comprising analyzing the received data to generate at least one instruction and transmitting the at least one instruction.

17. The method of claim 14 further comprising analyzing the received data and generating predictive information.

18. The method of claim 14 further comprising analyzing the received data and generating quantitative information.

19. The method of claim 14 wherein the at least one unit or stream is not in direct fluid communication with the conversion process.

* * * * *